(12) United States Patent
Naya et al.

(10) Patent No.: US 6,340,448 B1
(45) Date of Patent: Jan. 22, 2002

(54) SURFACE PLASMON SENSOR

(75) Inventors: Masayuki Naya; Masami Hatori, both of Kanagawa-ken (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/245,068

(22) Filed: Feb. 5, 1999

(30) Foreign Application Priority Data

| Feb. 5, 1998 | (JP) | ............................................. 10-024147 |
| Sep. 14, 1998 | (JP) | ............................................. 10-259577 |

(51) Int. Cl.$^7$ .............................................. G01N 21/01
(52) U.S. Cl. ................................. 422/82.11; 422/82.05; 356/445
(58) Field of Search ........................... 422/82.05, 82.11; 436/164, 165; 356/445, 447; 359/332

(56) References Cited

U.S. PATENT DOCUMENTS

| 4,169,676 | A |   | 10/1979 | Kaiser ............................ 356/39 |
| 5,712,705 | A | * | 1/1998 | Fattinger et al. ............... 356/354 |
| 5,907,408 | A | * | 5/1999 | Naya et al. ..................... 356/445 |
| 5,917,607 | A | * | 6/1999 | Naya ............................... 356/445 |
| 5,923,031 | A | * | 7/1999 | Naya ............................ 250/227.25 |
| 5,926,284 | A | * | 7/1999 | Naya et al. ..................... 356/445 |
| 6,208,422 | B1 | * | 3/2001 | Naya ............................... 356/445 |

FOREIGN PATENT DOCUMENTS

| JP | 6-167443 | 6/1994 |
| WO | 92/01217 | 1/1992 |

* cited by examiner

Primary Examiner—Maureen M. Wallenhorst
(74) Attorney, Agent, or Firm—Sughrue Mion, PLLC

(57) ABSTRACT

A surface plasmon sensor is formed by a dielectric block, a metal film which is formed on one face of the dielectric block and is brought into contact with a sample, a light source emitting a light beam, an optical system which causes the light beam to enter the dielectric block so that the light beam is reflected in total reflection at the interface of the dielectric block and the metal film and various angles of incidence of the light beam to the interface of the dielectric block and the metal film including an angle of incidence at which surface plasmon is generated can be obtained, and a photodetector which is able to detect the intensity of the light beam reflected in total reflection from the interface for the various angles of incidence. A laser provided with an oscillation wavelength stabilizing system for stabilizing the wavelength at which the laser oscillates is used as the light source.

36 Claims, 13 Drawing Sheets

F I G. 13
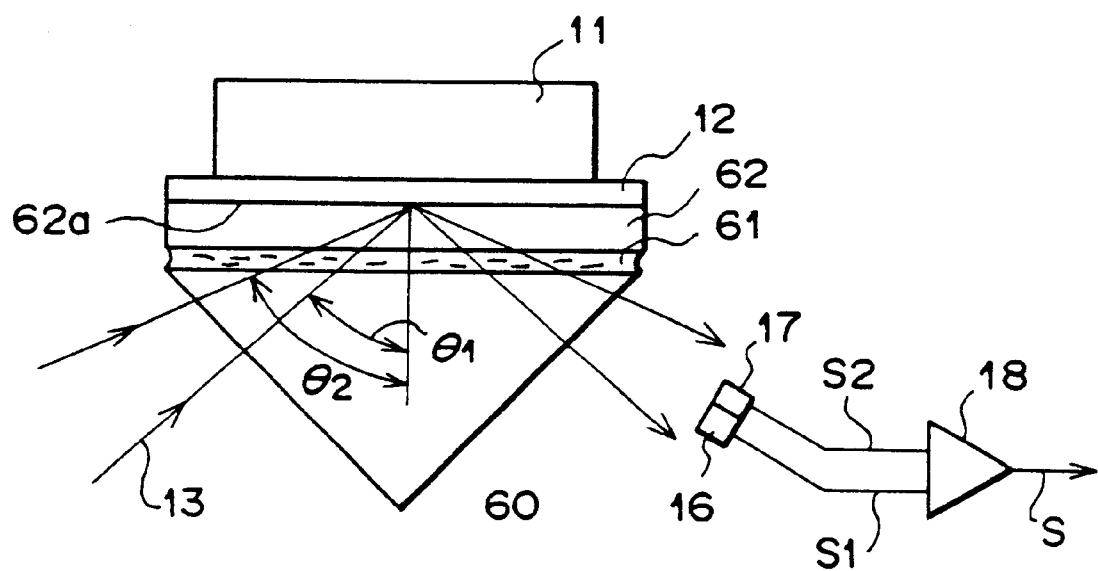

SURFACE PLASMON SENSOR

BACKGROUND OF THE INVENTION

1. Field of the Invention

This invention relates to a surface plasmon sensor for quantitatively analyzing a material in a sample utilizing generation of surface plasmon, and more particularly to a surface plasmon sensor in which the light source is improved to improve accuracy in analysis.

2. Description of the Related Art

In metal, free electrons vibrate in a group to generate compression waves called plasma waves. The compression waves generated in a metal surface are quantized into surface plasmon.

There have been proposed various surface plasmon sensors for quantitatively analyzing a material in a sample utilizing a phenomenon that such surface plasmon is excited by light waves. Among those, one employing a system called "Kretschmann configuration" is best known. See, for instance, Japanese Unexamined Patent Publication No. 6(1994)-167443.

The plasmon sensor using the Kretschmann configuration basically comprises a dielectric block shaped, for instance, like a prism, a metal film which is formed on one face of the dielectric block and is brought into contact with a sample, a light source emitting a light beam, an optical system which causes the light beam to enter the dielectric block so that the light beam is reflected in total reflection at the interface of the dielectric block and the metal film and various angles of incidence of the light beam to the interface of the dielectric block and the metal film including an angle of incidence at which surface plasmon is generated can be obtained, and a photodetector means which is able to detect the intensity of the light beam reflected in total reflection from the interface for the various angles of incidence.

In order to obtain various angles of incidence of the light beam to the interface, a relatively thin incident light beam may be caused to impinge upon the interface while deflecting the incident light beam or a relatively thick incident light beam may be caused to converge on the interface so that components of the incident light beam impinge upon the interface at various angles. In the former case, the light beam which is reflected from the interface at an angle which varies as the incident light beam is deflected may be detected by a photodetector which is moved in synchronization with deflection of the incident light beam or by an area sensor extending in the direction in which reflected light beam is moved as a result of deflection. In the latter case, an area sensor which extends in directions so that all the components of light reflected from the interface at various angles can be detected by the area sensor may be used.

In such a plasmon sensor, when a light beam impinges upon the metal film at a particular angle of incidence θsp not smaller than the angle of total internal reflection, evanescent waves having an electric field distribution are generated in the sample in contact with the metal film and surface plasmon is excited in the interface between the metal film and the sample. When the wave vector of the evanescent waves is equal to the wave number of the surface plasmon and wave number matching is established, the evanescent waves and the surface plasmon resonate and light energy is transferred to the surface plasmon, whereby the intensity of light reflected in total reflection from the interface of the dielectric block and the metal film sharply drops.

When the wave number of the surface plasmon can be known from the angle of incidence θsp at which the phenomenon of attenuation in total reflection takes place, the dielectric constant of the sample can be obtained. That is, $$Ksp(\tilde{\omega}) = \frac{\tilde{\omega}}{c} \sqrt{\frac{\epsilon_m(\tilde{\omega})\epsilon_s}{\epsilon_m(\tilde{\omega}) + \epsilon_s}}$$

wherein Ksp represents the wave number of the surface plasmon, ω represents the angular frequency of the surface plasmon, c represents the speed of light in a vacuum, and $\epsilon m$ and $\epsilon s$ respectively represent the dielectric constants of the metal and the sample.

When the dielectric constant $\epsilon s$ of the sample is known, the concentration of a specific material in the sample can be determined on the basis of a predetermined calibration curve or the like. Accordingly, a specific component in the sample can be quantitatively analyzed by detecting the angle of incidence θsp at which the intensity of light reflected in total reflection from the interface of the prism and the metal film sharply drops.

In the conventional plasmon sensor of the type described above, there has been generally used a laser as the light source. Especially when a single mode laser is used, the curve of attenuation in total reflection becomes sharper and a high sensitive measurement can be realized. However even such a laser is used, an accuracy of measurement cannot be always high.

SUMMARY OF THE INVENTION

In view of the foregoing observations and description, the primary object of the present invention is to provide a surface plasmon sensor in which a sufficiently high accuracy of measurement can be realized.

The surface plasmon sensor of the present invention comprises a dielectric block, a metal film, a light source emitting a light beam, an optical system, and a photodetector means which are described above and is characterized in that a laser provided with an oscillation wavelength stabilizing means for stabilizing the wavelength at which the laser oscillates is used as the light source.

A semiconductor laser, which is advantageous in reducing the overall size of system, can be suitably used as the laser. In this case, the oscillation wavelength stabilizing means may comprise, for instance, a beam feedback optical system which feeds a part of a laser beam emitted from the semiconductor laser back to the semiconductor laser and a wavelength selector such as a grating or a band pass filter which selects the wavelength of the laser beam to be fed back to the semiconductor laser.

In the case where a bulk grating is used as the wavelength selector, the beam feedback optical system may comprise a beam splitter means which is disposed on the optical path of the laser beam traveling from the semiconductor laser to the dielectric block and splits a part of the laser beam and a reflective grating which reflects the laser beam split by the beam splitter means to retrace its path, and the reflective grating may double as the wavelength selector.

It is possible to form the beam feedback optical system and the wavelength selector by a partial reflection type grating which is disposed on the optical path of the laser beam traveling from the semiconductor laser to the dielectric block and reflects a part of the laser beam toward the semiconductor laser.

Further it is possible to form the beam feedback optical system and the wavelength selector by a reflective grating which reflects toward the semiconductor laser a rearward laser beam emitted from the semiconductor laser in the direction opposite to the laser beam traveling from the semiconductor laser to the dielectric block.

Further, the oscillation wavelength stabilizing means may comprise a combination of a beam feedback optical system comprising a beam splitter means which is disposed on the optical path of the laser beam traveling from the semiconductor laser to the dielectric block and splits a part of the laser beam and a mirror which reflects the laser beam split by the beam splitter means to retrace its path and a narrow-band pass filter disposed on the optical path of the laser beam between the mirror and the semiconductor laser.

Further, the oscillation wavelength stabilizing means may comprise a combination of a beam feedback optical system comprising a half-silvered mirror which is disposed on the optical path of the laser beam traveling from the semiconductor laser to the dielectric block and reflects a part of the laser beam toward the semiconductor laser and a narrow-band pass filter disposed on the optical path of the laser beam between the half-silvered mirror and the semiconductor laser.

Further, the oscillation wavelength stabilizing means may comprise a combination of a beam feedback optical system comprising a mirror which reflects toward the semiconductor laser a rearward laser beam emitted from the semiconductor laser in the direction opposite to the laser beam traveling from the semiconductor laser to the dielectric block and a narrow-band pass filter disposed on the optical path of the rearward laser beam between the mirror and the semiconductor laser.

As the wavelength selector, may be used a fiber grating comprising an optical fiber which has a plurality of refractive index varying portions formed in the core at regular intervals and reflects and diffracts a laser beam.

In the case where a fiber grating is used as the wavelength selector, the beam feedback optical system may comprise a beam splitter means which is disposed on the optical path of the laser beam traveling from the semiconductor laser to the dielectric block and splits a part of the laser beam and a fiber grating which reflects the laser beam split by the beam splitter means to retrace its path, and the fiber grating may double as the wavelength selector.

It is possible to form the beam feedback optical system and the wavelength selector by a partial reflection type fiber grating which is disposed on the optical path of the laser beam traveling from the semiconductor laser to the dielectric block and reflects a part of the laser beam toward the semiconductor laser.

Further it is possible to form the beam feedback optical system and the wavelength selector by a fiber grating which reflects toward the semiconductor laser a rearward laser beam emitted from the semiconductor laser in the direction opposite to the laser beam traveling from the semiconductor laser to the dielectric block.

It is possible to stabilize the oscillation wavelength of the laser without feeding back the laser beam. For example, the oscillation wavelength of the laser can be stabilized by use of a DFB (distributed feedback) laser or a DBR (distributed Bragg reflector) laser as the light source.

Further the oscillation wavelength stabilizing means need not be limited to those described above and, for instance, a means for electrically controlling the laser drive current and/or the temperature of the laser may be used as the oscillation wavelength stabilizing means.

We have found that the problem that it is difficult to obtain a high accuracy in measurement in the conventional plasmon sensor using a laser as the light source is due to fluctuation in the oscillation wavelength of the laser. That is, fluctuation in the oscillation wavelength of the laser affects the condition of generation of the surface plasmon, which generates noise in the surface plasmon detecting signal (a signal representing the intensity of light reflected in total reflection from the interface of the dielectric block and the metal film) and deteriorates the accuracy in measurement.

Accordingly, in the surface plasmon sensor of this embodiment, fluctuation in the oscillation wavelength of the laser can suppressed by the oscillation wavelength stabilizing means and generation of the aforesaid noise is suppressed, whereby the accuracy in measurement can be improved.

BRIEF DESCRIPTION OF THE DRAWINGS

FIG. 13 is a fragmentary side view showing a part of a surface plasmon sensor in accordance with an eleventh embodiment of the present invention.

DESCRIPTION OF THE PREFERRED EMBODIMENTS

Figure 1:
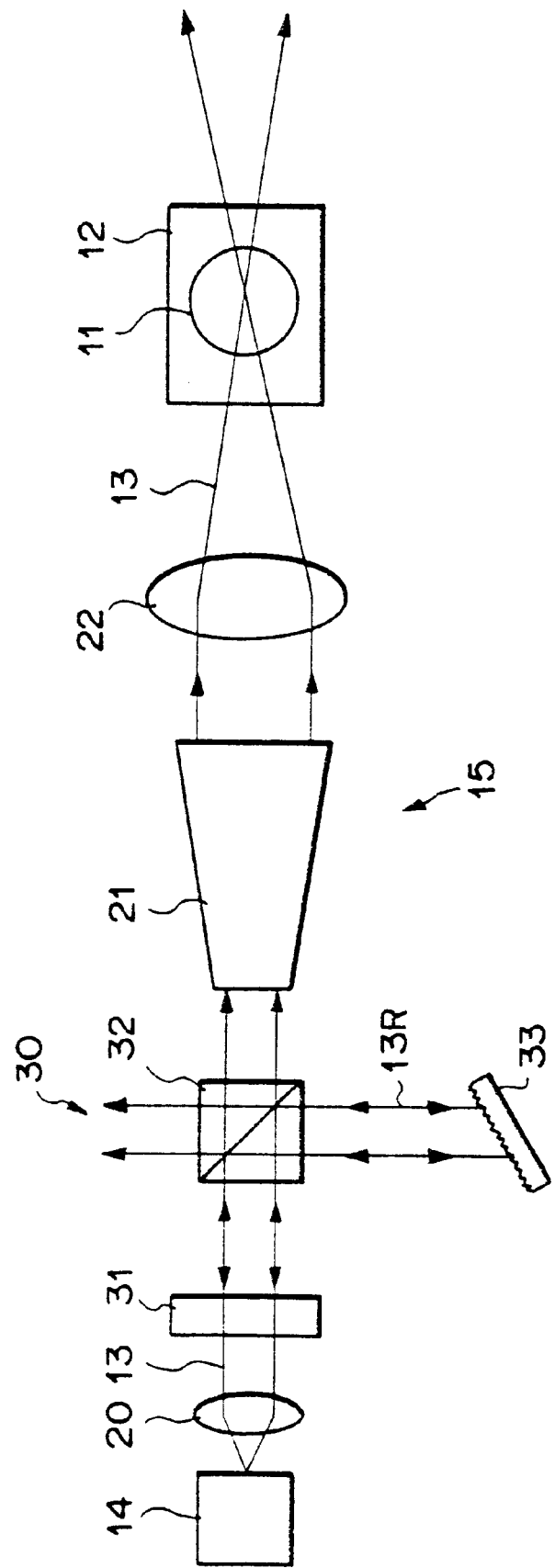
FIG. 1 is a plan view of a surface plasmon sensor in accordance with a first embodiment of the present invention.
Figure 2:
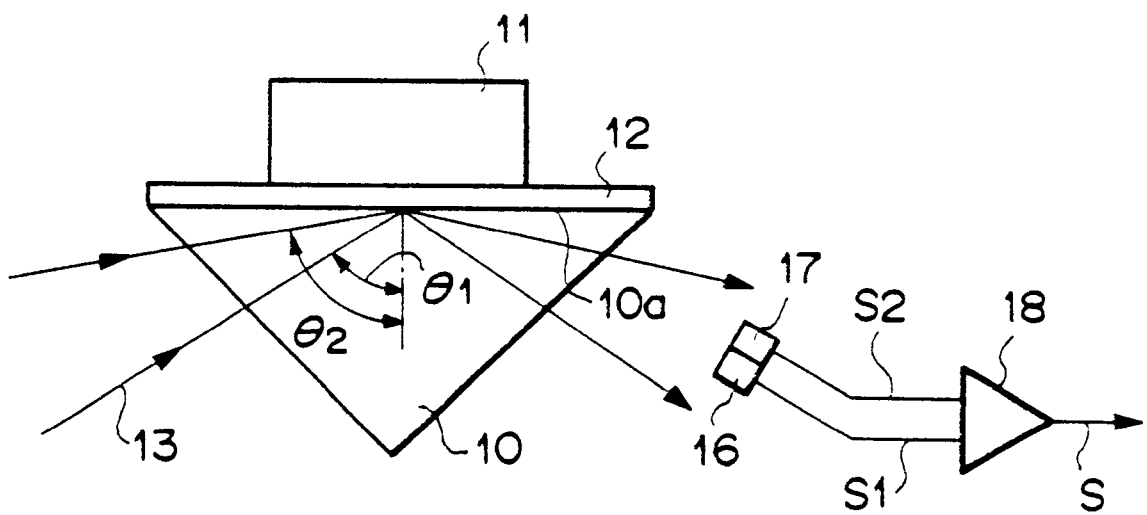
FIG. 2 is a fragmentary side view showing a part of the surface plasmon sensor.

In FIGS. 1 and 2, a surface plasmon sensor in accordance with a first embodiment of the present invention comprises a triangular prism 10 having a major axis extending in the vertical direction (as seen in FIG. 1), a metal film 12 such as of gold, silver or the like which is formed on one face (the upper face as seen in FIG. 1) of the prism 10 and brought into contact with a sample 11, a semiconductor laser 14 emitting a single light beam (laser beam) 13, an optical system 15 which causes the light beam 13 to enter the prism 10 so that various angles of incidence of the light beam 13 to the interface 10a of the prism 10 and the metal film 12 can be obtained, first and second photodetectors 16 and 17 which detects the amount of light of the light beam 13 reflected in total reflection from the interface 10a and a comparator 18 connected to the first and second photodetectors 16 and 17.

The optical system 15 comprises a collimator lens 20 which collimates the diverging light beam 13 emitted from the semiconductor laser 14, a beam expander 21 which expands the diameter of the collimated light beam 13 and a condenser lens 22 which converges the expanded light beam 13 on the interface 10a.

An oscillation wavelength stabilizing means 30 is disposed between the collimator lens 20 and the beam expander 21 as will be described later.

Since the light beam 13 is converged on the interface 10a by the condenser lens 22, the light beam 13 impinging upon the interface 10a contains components which impinge upon the interface 10a at various angles θ. In FIG. 2, θ1 denotes a minimum angle of incidence and θ2 denotes a maximum angle of incidence. The angle of incidence θ is made not smaller than an angle of total internal reflection. The light beam 13 is reflected in total reflection at the interface 10a and accordingly the reflected light beam 13 contains components which are reflected at the interface 10a at various angles.

The first and second photodetectors 16 and 17 may comprise, for instance, a two-segment photodiode. The first photodetector 16 detects the amount of light of the components of the light beam 13 reflected from the interface 10a at angles in a first reflecting angle range (relatively small angle range) and the second photodetector 17 detects the amount of light of the components of the light beam 13 reflected from the interface 10a at angles in a second reflecting angle range (relatively large angle range).

Analysis of a sample by the surface plasmon sensor of this embodiment will be described, hereinbelow.

That is, the sample 11 is placed in contact with the metal film 12. When effecting analysis, a light beam 13 converged in the manner described above is caused to impinge upon the metal film 12. The light beam 13 reflected in total reflection from the interface 10a of the metal film 12 and the prism 10 is detected by the first and second photodetectors 16 and 17.

Light amount signals S1 and S2 respectively output from the first and second photodetectors 16 and 17 are input into the comparator 18 and the comparator 18 outputs a differential signal S representing the difference between the light amount signals S1 and S2.

Figure 3A:
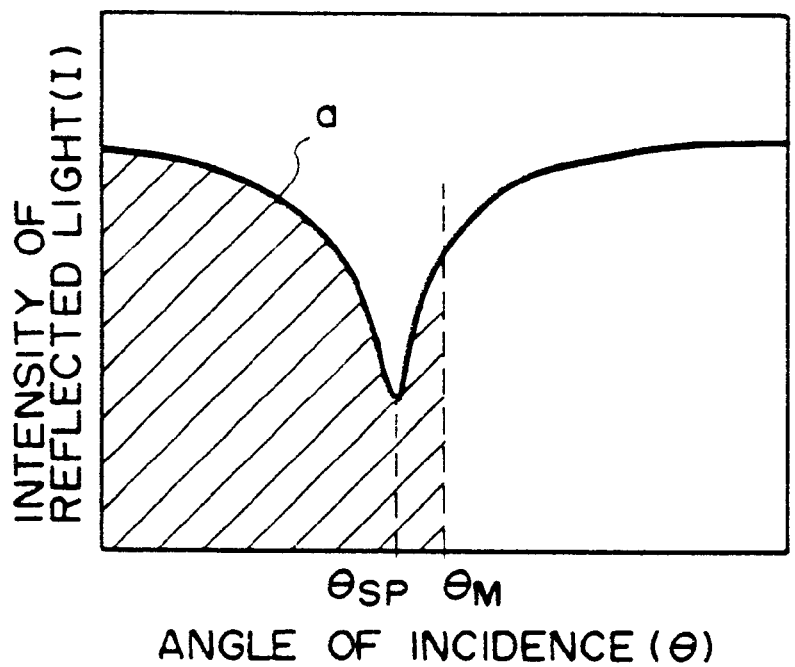
FIGS. 3A and 3B are graphs showing the relation between the angle of incidence of a light beam and the output of the photodetector means.
Figure 3B:
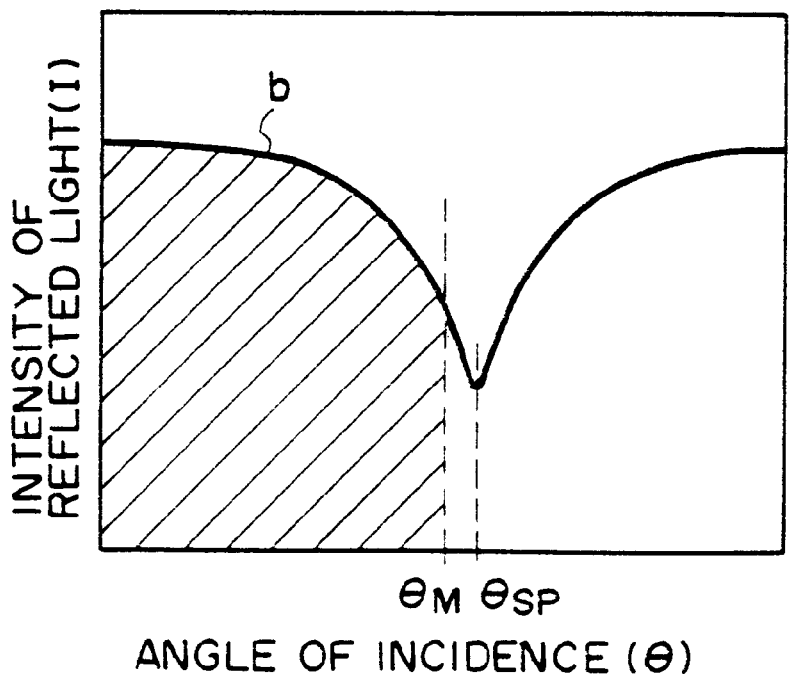

As described in detail before, a light beam impinging upon the interface 10a at a particular angle of incidence θsp excites surface plasmon in the interface 10a, and the intensity I of the light reflected from the interface 10a at an angle corresponding to the angle θsp greatly drops. That is, the relation between the angle of incidence θ of the light beam to the interface 10a and the intensity I of the reflected light is substantially as shown by curve a in FIG. 3A or curve b in FIG. 3B. When the value of the particular angle of incidence θsp and the relation between the angle of incidence θ of the light beam to the interface 10a and the intensity I of the reflected light are known, a specific material in the sample 11 can be quantitatively analyzed. This will be described in detail hereinbelow.

For example, when the first and second reflecting angle ranges are continuous and the reflecting angle at the boundary therebetween is θM, the first photodetector 16 detects the amount of light of the components of the light beam 13 impinges upon the interface 10a at angles smaller than θM and the second photodetector 17 detects the amount of light of the components of the light beam 13 impinges upon the interface 10a at angles larger than θM. That is, the first photodetector 16 detects light in the range shown by the hatched portion in each of FIGS. 3A and 3B. The amount of light detected by the first photodetector 16 is larger in the case shown in FIG. 3B than the case shown in FIG. 3A. Conversely, the amount of light detected by the second photodetector 17 is smaller in the case shown in FIG. 3B than the case shown in FIG. 3A. The difference between the amount of light detected by the first photodetector 16 and that detected by the second photodetector 17 is specific according to the relation between the angle of incidence θ and the intensity I of the reflected light.

Accordingly by referring to a standard curve which has been determined for each sample, the value of the particular angle of incidence θ sp and the relation between the angle of incidence θ of the light beam to the interface 10a and the intensity I of the reflected light for the sample 11 to be analyzed can be estimated on the basis of the differential signal S representing the difference between the light amount signals S1 and S2 respectively output from the first and second photodetectors 16 and 17, whereby a specific material in the sample 11 can be quantitatively analyzed.

Also in the case where the first and second reflecting angle ranges are not continuous, the difference between the amount of light detected by the first photodetector 16 and that detected by the second photodetector 17 is specific according to the relation between the angle of incidence θ and the intensity I of the reflected light and accordingly a specific material in the sample 11 can be quantitatively analyzed in the same manner.

The oscillation wavelength stabilizing means 30 will be described, hereinbelow. In this embodiment, the oscillation wavelength stabilizing means 30 comprises a λ/2 plate 31 which controls the polarization of the light beam 13, a beam splitter 32 which reflects a part of the light beam 13 passing through the λ/2 plate 31 and transmits the other part of the light beam 13 and a reflective grating 33 which disposed to receive the light beam 13R reflected by the beam splitter 32.

The light beam 13R impinging upon the reflective grating 33 is selected by wavelength into a beam having a very narrow spectral bandwidth by the grating 33 and the light beam thus obtained is reflected to retrace the path of the light beam 13R. The light beam 13R is fed back to the semiconductor laser 14 through the beam splitter 32 and the λ/2 plate 31. Thus an external resonator is formed by the rear end face (the left end face as shown in FIG. 1) of the semiconductor laser 14 and the reflective grating 33 and the oscillation wavelength of the semiconductor laser 14 is locked to the wavelength selected by the reflective grating 33.

When the oscillation wavelength of the semiconductor laser 14 is thus stabilized, generation of noise in the differential signal S due to fluctuation in the oscillation wavelength is prevented and the accuracy in measurement can be improved.

Second to eleventh embodiments of the present invention will be described with reference to FIGS. 4 to 13, hereinbelow. The surface plasmon sensors of these embodiments differ from that of the first embodiment only the structure of the oscillation wavelength stabilizing means. Accordingly in FIGS. 4 to 13, the elements analogous to those shown in FIGS. 1 and 2 are given the same reference numerals and only the oscillation wavelength stabilizing means will be described, hereinbelow.

Figure 4:
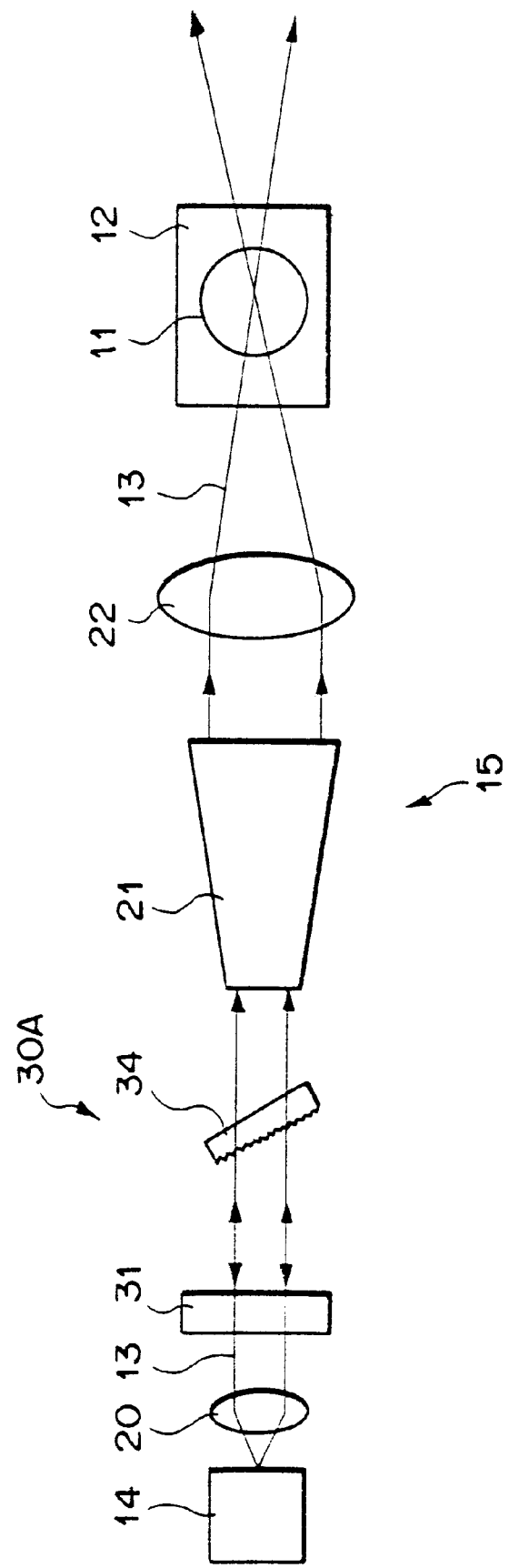
FIG. 4 is a plan view of a surface plasmon sensor in accordance with a second embodiment of the present invention.

In FIG. 4, the oscillation wavelength stabilizing means 30A in the second embodiment is formed by a partial reflection type grating 34 which doubles the beam feedback optical system and the wavelength selector. The partial reflection type grating 34 is disposed on the optical path of the light beam 13 traveling from the semiconductor laser 14 to the prism 10 and reflects a part of the light beam 13 toward the semiconductor laser 14.

The reflected light beam 13 is fed back to the semiconductor laser 14 and the oscillation wavelength of the semiconductor laser 14 is locked to the wavelength selected by the partial reflection type grating 34.

Figure 5:
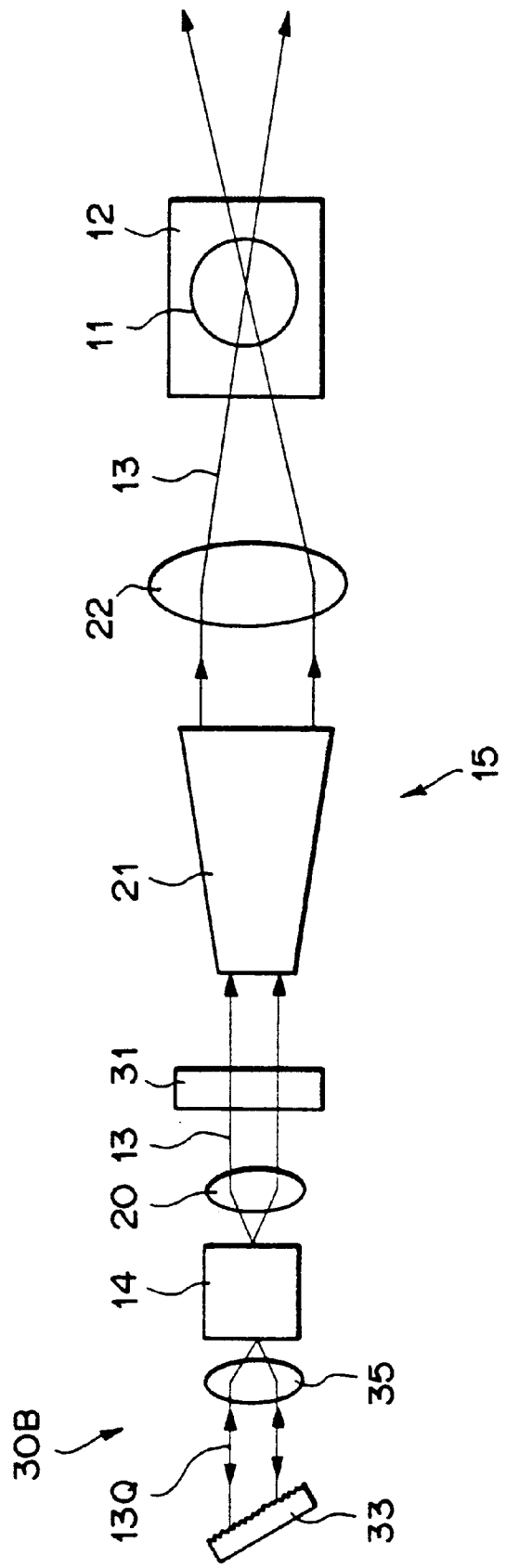
FIG. 5 is a plan view of a surface plasmon sensor in accordance with a third embodiment of the present invention.

In FIG. 5, the oscillation wavelength stabilizing means 30B in the third embodiment is formed by a reflective grating 33 and a collimator lens 35.

The reflective grating 33 forms a beam feedback optical system together with the collimator lens 35 and doubles as a wavelength selector. That is, a rearward light beam 13Q emitted from the semiconductor laser 14 in the direction opposite to the light beam traveling from the semiconductor laser 14 to the prism 10 is collimated by the collimator lens 35 and impinges upon the reflective grating 33.

The reflected light beam 13Q reflected by the reflective grating 33 is fed back to the semiconductor laser 14 and the oscillation wavelength of the semiconductor laser 14 is locked to the wavelength selected by the reflective grating 33.

Figure 6:
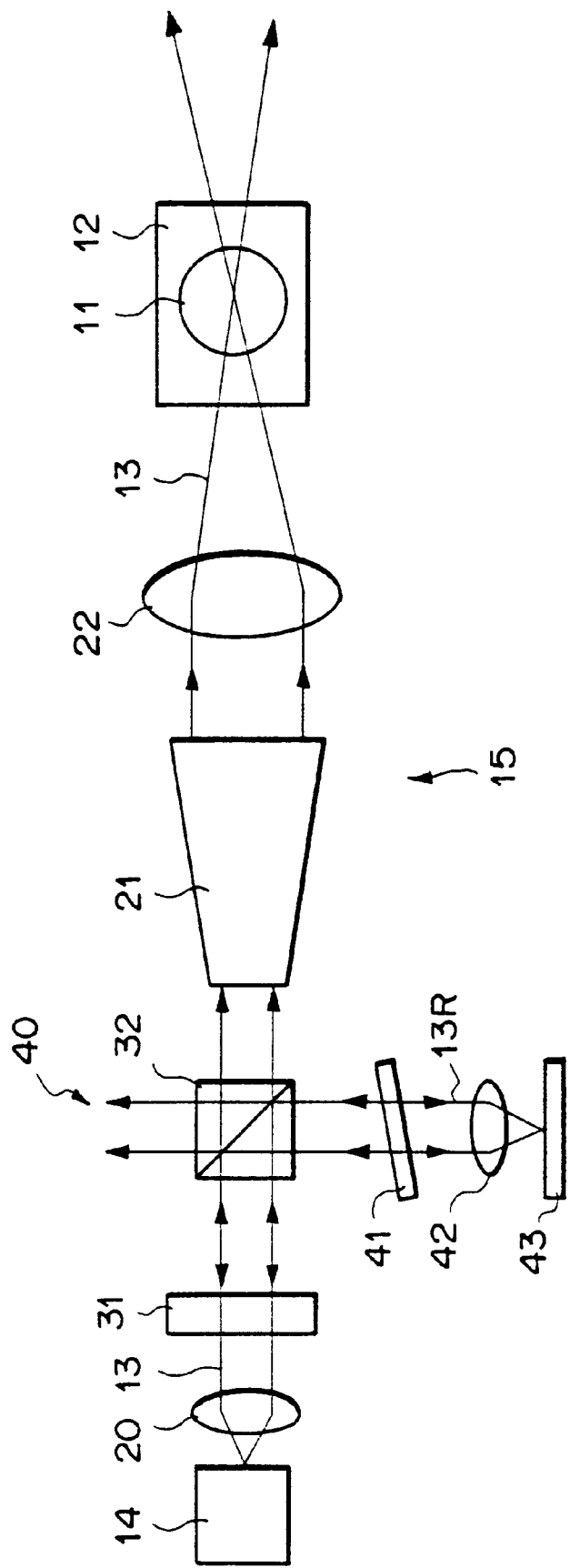
FIG. 6 is a plan view of a surface plasmon sensor in accordance with a fourth embodiment of the present invention.

In FIG. 6, the oscillation wavelength stabilizing means 40 in the fourth embodiment comprises a combination of a beam feedback optical system comprising a beam splitter 32 which is disposed on the optical path of the light beam 13 traveling from the semiconductor laser 14 to the prism 10 and splits a part of the laser beam 13, a narrow-band pass filter 41 which is disposed in a position where the light beam 13 split by the beam splitter 32 passes therethrough, a condenser lens 42 which converges the light beam 13R passing through the filter 41 and a mirror 43 on which the light beam 13R is converged by the condenser lens 42.

The light beam 13R is selected by wavelength into a beam having a very narrow spectral bandwidth by the filter 41 and the light beam thus obtained is reflected by the mirror 43 to retrace the path of the light beam 13R. The light beam is fed back to the semiconductor laser 14 through the beam splitter 32 and the λ/2 plate 31. Thus the oscillation wavelength of the semiconductor laser 14 is locked to the wavelength selected by the narrow-band pass filter 41.

A half-silvered mirror can be employed in place of the beam splitter 32.

Figure 7:
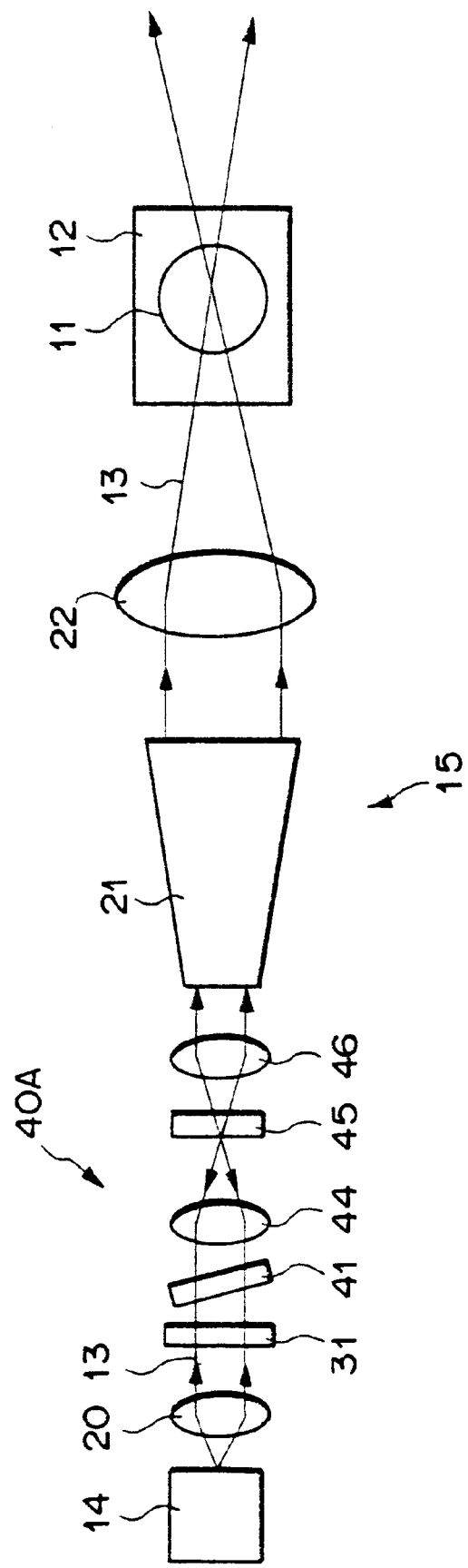
FIG. 7 is a plan view of a surface plasmon sensor in accordance with a fifth embodiment of the present invention.

In FIG. 7, the oscillation wavelength stabilizing means 40A in the fifth embodiment comprises a narrow-band pass filter 41, a condenser lens 44, a half-silvered mirror 45 and a collimator lens 46 which are disposed in this order on the optical path of the light beam 13 traveling from the semiconductor laser 14 to the prism 10.

The condenser lens 44 and the half-silvered mirror 45 forms a beam feedback optical system. That is, a part of the light beam 13 is reflected by the half-silvered mirror 45 which is disposed so that the light beam 13 is converged thereon by the condenser lens 44 and is fed back to the semiconductor laser 14.

The light beam 13 is selected by wavelength into a beam having a very narrow spectral bandwidth by the filter 41 and the light beam thus obtained is fed back to the semiconductor laser 14. Thus the oscillation wavelength of the semiconductor laser 14 is locked to the wavelength selected by the narrow-band pass filter 41.

Figure 8:
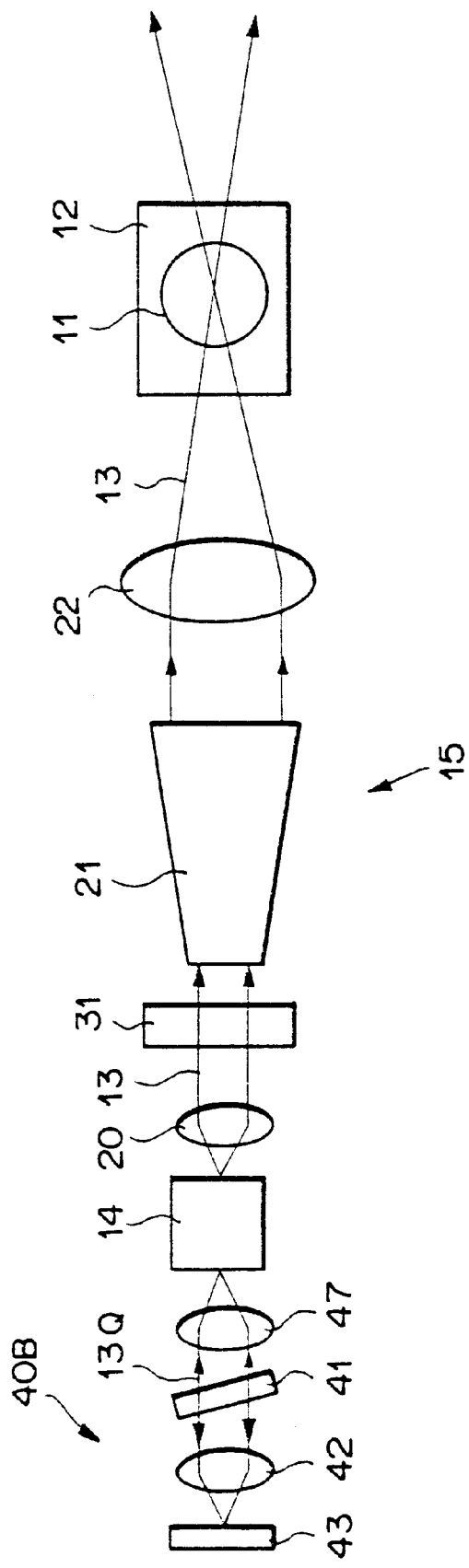
FIG. 8 is a plan view of a surface plasmon sensor in accordance with a sixth embodiment of the present invention.

In FIG. 8, the oscillation wavelength stabilizing means 40B in the sixth embodiment comprises a collimator lens 47 which collimates a rearward light beam 13Q from the semiconductor laser 14, a narrow-band pass filter 41 through which the collimated rearward light beam 13Q passes, a condenser lens 42 which converges the light beam 13Q passing through the filter 41 and a mirror 43 on which the light beam 13Q is converged by the condenser lens 42.

The condenser lens 42 and the mirror 43 form a beam feedback optical system and the narrow-band filter 41 forms a wavelength selector. That is, the light beam 13Q is selected by wavelength into a beam having a very narrow spectral bandwidth by the filter 41 and the light beam thus obtained is fed back to the semiconductor laser 14. Thus the oscillation wavelength of the semiconductor laser 14 is locked to the wavelength selected by the narrow-band pass filter 41.

Figure 9:
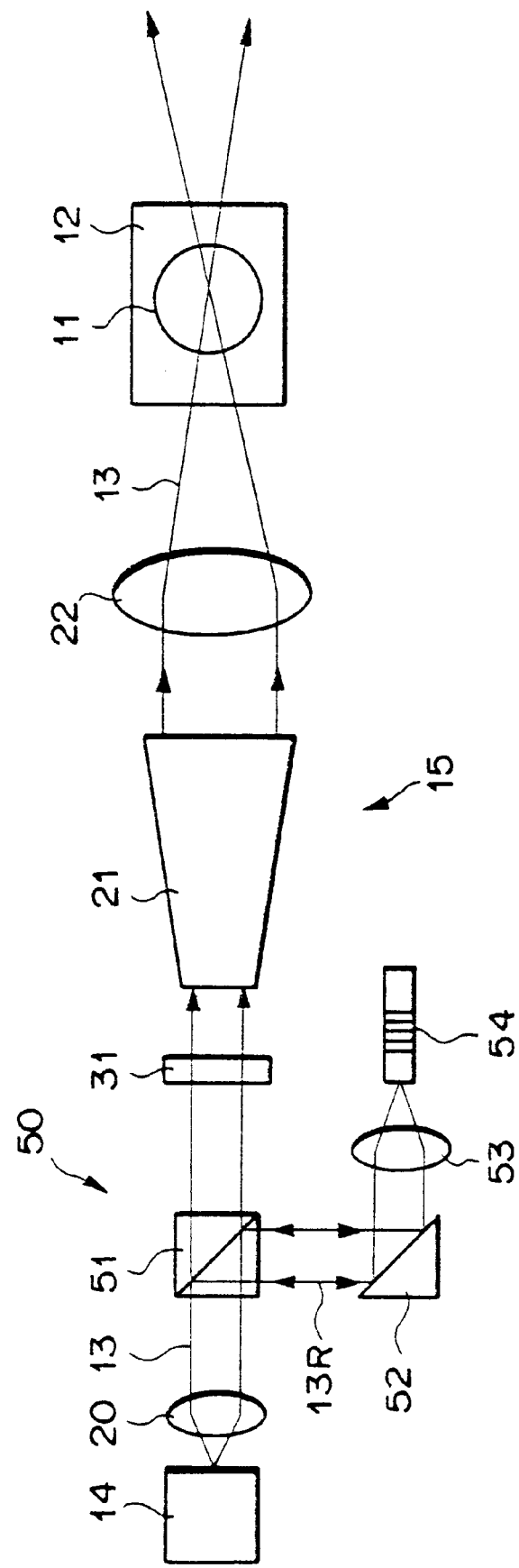
FIG. 9 is a plan view of a surface plasmon sensor in accordance with a seventh embodiment of the present invention.

In FIG. 9, the oscillation wavelength stabilizing means 50 in the seventh embodiment comprises a beam splitter 51 which is disposed on the optical path of the light beam 13 traveling from the semiconductor laser 14 to the prism 10 and splits a part of the laser beam 13, a mirror 52 which reflects the light beam 13R split by the beam splitter 51, a condenser lens 53 which converges the light beam 13R reflected by the mirror 52 and a reflective fiber grating 54 on one end face of which the light beam 13R is converged by the condenser lens 53.

The reflective fiber grating 54 comprises a clad and a core which has a refractive index higher than that of the clad and is embedded in the clad. A plurality of refractive index varying portions are formed in the core at regular intervals. For example, the reflective fiber grating 54 is formed by forming interference fringes in the core of an optical communication fiber (125 μm in the outer diameter of the clad and about 10 μm in the diameter of the core) by two-beam interference with excimer laser beams in ultraviolet region, thereby changing (increasing) the refractive indices of the parts of the core exposed to the leaser beams. It is supposed that the change in the refractive index is caused by chemical change of germanium oxide, with which the core is doped, upon exposure to ultraviolet rays.

The light beam 13R condensed by the condenser lens 53 enters the core through the end face of the reflective fiber grating 54 and propagates through the core. The aforesaid refractive index varying portions forms a grating along the direction in which the light beam 13R propagates. The grating reflects and diffracts only light of a specific wavelength corresponding to the period of the refractive index varying portions out of the light beam 13R propagating through the grating and feeds back the light of the specific wavelength back to the semiconductor laser 14, whereby the oscillation wavelength of the semiconductor laser 14 is locked to the wavelength selected by the reflective fiber grating 54.

Figure 10:
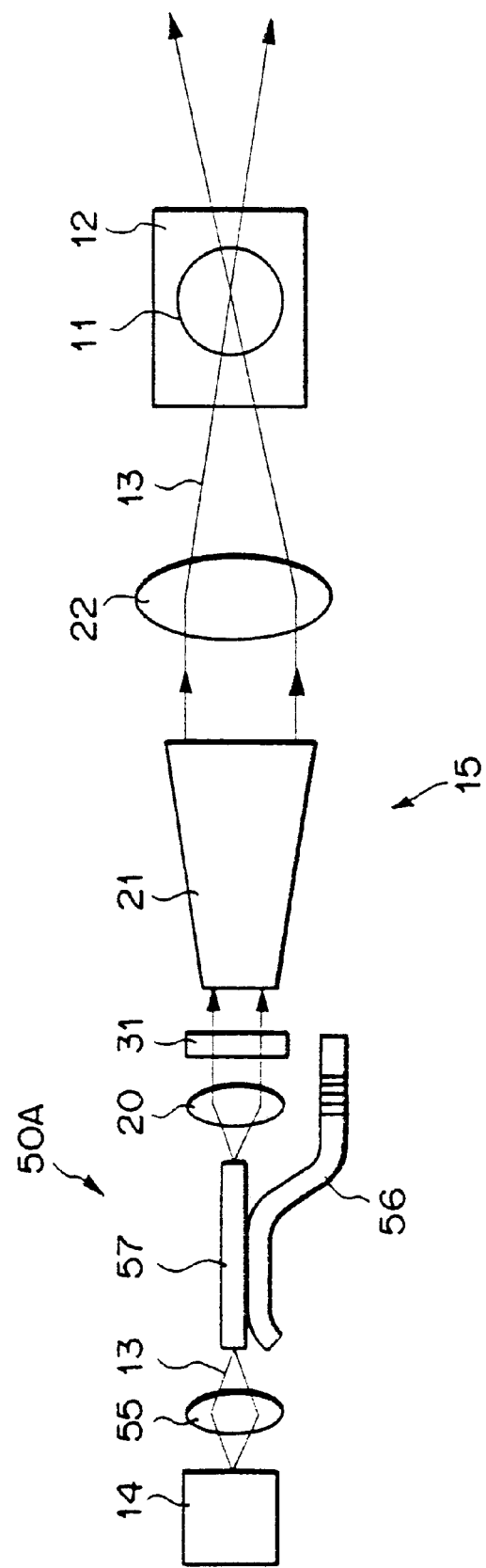
FIG. 10 is a plan view of a surface plasmon sensor in accordance with an eighth embodiment of the present invention.

In FIG. 10, the oscillation wavelength stabilizing means 50A in the eighth embodiment comprises a condenser lens 55 which condenses the light beam 13 emitted from the semiconductor laser 14 and first and second fibers 56 and 57 which form a fiber coupler. The first fiber 56 has refractive index varying portions such as those described above and the second fiber 57 is jointed to the first fiber 56.

A part of the light beam 13 which enters the second fiber 57 through an end face of the second fiber 57 and propagates along the second fiber 57 is transferred to the first fiber 56. The part of the light beam 13 which propagates through the second fiber 57 and emitted through the other end face of the second fiber 57 is used for analysis of the sample.

On the other hand, the part of the light beam 13 transferred to the first fiber 56 propagates along the first fiber 56 and is reflected and refracted by the refractive index varying portions. The part of the light beam 13 reflected and refracted by the refractive index varying portions is fed back to the semiconductor laser 14 through the condenser lens 55, whereby the oscillation wavelength of the semiconductor laser 14 is locked to the wavelength selected by the first fiber 56.

Figure 11:
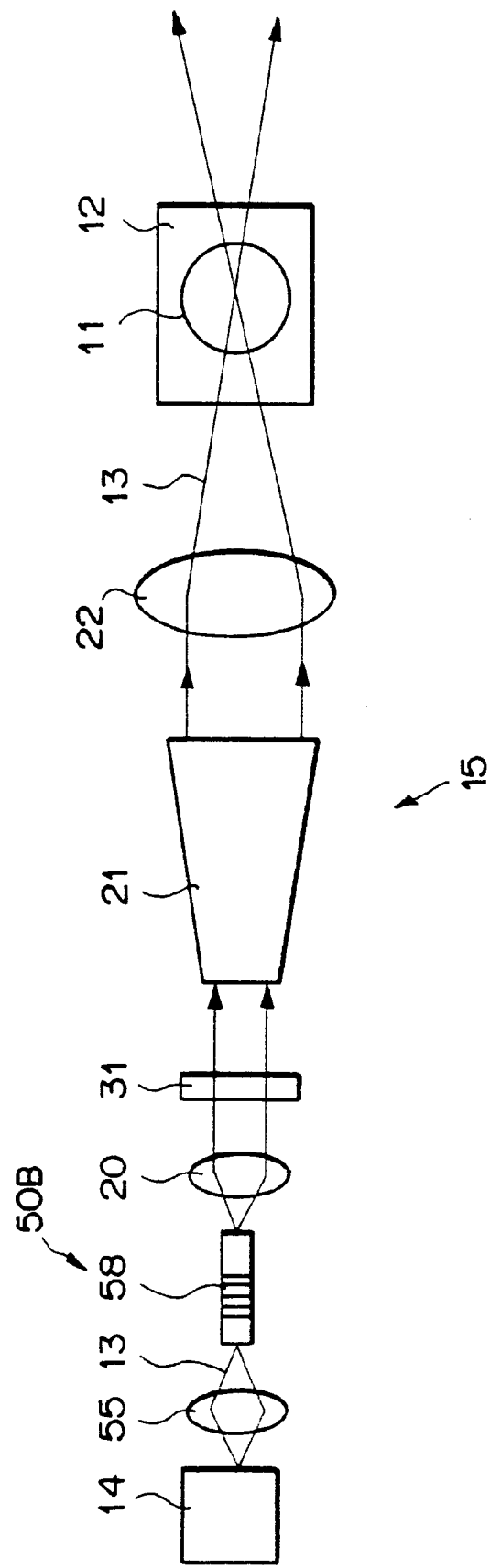
FIG. 11 is a plan view of a surface plasmon sensor in accordance with a ninth embodiment of the present invention.

In FIG. 11, the oscillation wavelength stabilizing means 50B in the ninth embodiment comprises a condenser lens 55 which condenses the light beam 13 emitted from the semiconductor laser 14 and a partial reflection type fiber grating 58 which is positioned so that the light beam 13 condensed by the condenser lens 55 is converged on an end face thereof.

The partial reflection type fiber grating 58 is basically of the same structure as the reflective fiber grating 54 and reflects and diffracts only light of a specific wavelength corresponding to the period of the refractive index varying portions out of the light beam 13 propagating through the core and feeds back the light of the specific wavelength back to the semiconductor laser 14, whereby the oscillation wavelength of the semiconductor laser 14 is locked to the wavelength selected by the partial reflection type fiber grating 58.

The part of the light beam 13 which passes through the partial reflection type fiber grating 58 is used for analysis of the sample.

Figure 12:
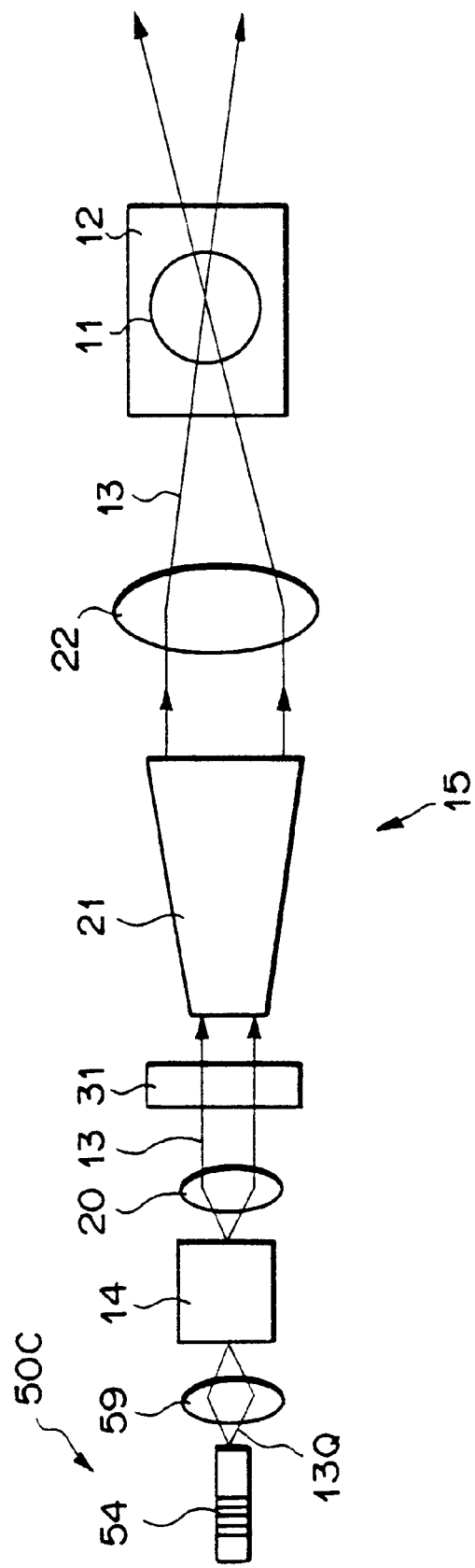
FIG. 12 is a plan view of a surface plasmon sensor in accordance with a tenth embodiment of the present invention.

In FIG. 12, the oscillation wavelength stabilizing means 50C in the tenth embodiment comprises a condenser len5947 which converges a rearward light beam 13Q emitted from the semiconductor laser 14 and a reflective fiber grating 54 positioned so that the light beam 13Q is converged on one end face thereof by the condenser lens 59.

The part of the rearward light beam 13Q reflected by the reflective fiber grating 54 is fed back to the semiconductor laser 14, whereby the oscillation wavelength of the semiconductor laser 14 is locked to the wavelength selected by the reflective fiber grating 54.

The surface plasmon sensor in accordance with the eleventh embodiment of the present invention shown in FIG. 13 basically differs from that shown in FIG. 2 in that the metal film 12 is formed on a dielectric block 62 of a glass which is substantially rectangular in shape and is connected to the upper face of a prism 60 by way of refractive index matching fluid 61.

In this plasmon sensor, the light beam 13 is caused to impinge upon the interface 62a of the dielectric block 62 and the metal film 12 through the prism 60 so that the light beam 13 is reflected in total reflection by the interface 62a. The dielectric block 62 and the prism 60 are formed of the same material and are connected by the refractive index matching fluid 61 which is equal to the material of the dielectric block 62 and the prism 60 in refractive index. Accordingly the system of the dielectric block 62 and the prism 60 is optically equivalent to the single prism 10.

Though, in the embodiments described above, the oscillation wavelength of the laser is stabilized by feedback of the laser beam, it is possible to stabilize the oscillation wavelength of the laser without feeding back the laser beam. For example, a laser such as a DFB (distributed feedback) laser or a DBR (distributed Bragg reflector) laser or the like which has an oscillation wavelength stabilizing means per se may be used as the light source.

Further the oscillation wavelength stabilizing means may be a means for electrically controlling the laser drive current and/or the temperature of the laser.

Further the present invention can be applied also to a plasmon sensor in which a layer of a material which is specifically coupled to a material to be measured is formed on a metal film and only a specific material is detected (e.g., a plasmon sensor for detecting antigen-antibody reaction), a plasmon sensor which measures the two-dimensional distribution of physical properties of a sample placed on a metal film, and the like.

What is claimed is:

1. A surface plasmon sensor comprising:
    a dielectric block,
    a metal film which is formed on one face of the dielectric block and is brought into contact with a sample,
    a light source emitting a light beam,
    an optical system which causes the light beam to enter the dielectric block so that the light beam is reflected in total reflection at an interface of the dielectric block and the metal film and various angles of incidence of the light beam to the interface of the dielectric block and the metal film including an angle of incidence at which surface plasmon is generated can be obtained, and
    a photodetector means which is able to detect the intensity of the light beam reflected in total reflection from the interface for the various angles of incidence,
    wherein the improvement comprises that
        a laser provided with an oscillation wavelength stabilizing means for stabilizing the wavelength at which the laser oscillates is used as the light source.

2. A surface plasmon sensor as defined in claim 1 in which the laser is a semiconductor laser and the light beam comprises a laser beam, and the oscillation wavelength stabilizing means comprises a beam feedback optical system which feeds a part of the laser beam emitted from the semiconductor laser back to the semiconductor laser and a wavelength selector which selects the wavelength of the laser beam to be fed back to the semiconductor laser.

3. A surface plasmon sensor as defined in claim 2 in which the wavelength selector comprises a bulk grating.

4. A surface plasmon sensor as defined in claim 3 in which the beam feedback optical system comprises:
    a beam splitter means which is disposed on an optical path of the laser beam traveling from the semiconductor laser to the dielectric block and splits a part of the laser beam; and
    a reflective grating which reflects the part of the laser beam split by the beam splitter means to retrace its path, the reflective grating doubling as the wavelength selector.

5. A surface plasmon sensor as defined in claim 3 in which the beam feedback optical system and the wavelength selector are formed by a partial reflection type grating which is disposed on an optical path of the laser beam traveling from the semiconductor laser to the dielectric block and reflects a part of the laser beam toward the semiconductor laser.

6. A surface plasmon sensor as defined in claim 3 in which the beam feedback optical system and the wavelength selector are formed by a reflective grating which reflects toward the semiconductor laser a rearward laser beam emitted from the semiconductor laser in the direction opposite to the laser beam traveling from the semiconductor laser to the dielectric block.

7. A surface plasmon sensor as defined in claim 2 in which the wavelength selector comprises a narrow-band pass filter.

8. A surface plasmon sensor as defined in claim 7 in which the beam feedback optical system comprises:
    a beam splitter means which is disposed on an optical path of the laser beam traveling from the semiconductor laser to the dielectric block and splits a part of the laser beam; and a mirror which reflects the part of the laser beam split by the beam splitter means to retrace its path, wherein the narrow-band pass filter is disposed on an optical path of the laser beam between the mirror and the semiconductor laser.

9. A surface plasmon sensor as defined in claim 7 in which the beam feedback optical system comprises:

a half-silvered mirror which is disposed on an optical path of the laser beam traveling from the semiconductor laser to the dielectric block and reflects a part of the laser beam toward the semiconductor laser, wherein the narrow-band pass filter is disposed on an optical path of the laser beam between the half-silvered mirror and the semiconductor laser.

10. A surface plasmon sensor as defined in claim 7 in which the beam feedback optical system comprises:

a mirror which reflects toward the semiconductor laser a rearward laser beam emitted from the semiconductor laser in the direction opposite to the laser beam traveling from the semiconductor laser to the dielectric block, wherein the narrow-band pass filter is disposed on an optical path of the rearward laser beam between the mirror and the semiconductor laser.

11. A surface plasmon sensor as defined in claim 2 in which the wavelength selector comprises a fiber grating which comprises an optical fiber having a plurality of refractive index varying portions formed in a core at regular intervals and reflects and diffracts a laser beam.

12. A surface plasmon sensor as defined in claim 11 in which the beam feedback optical system comprises:

a beam splitter means which is disposed on an optical path of the laser beam traveling from the semiconductor laser to the dielectric block and splits a part of the laser beam; and a fiber grating which reflects the part of the laser beam split by the beam splitter means to retrace its path, the fiber grating doubling as the wavelength selector.

13. A surface plasmon sensor as defined in claim 11 in which the beam feedback optical system and the wavelength selector are formed by a partial reflection type fiber grating which is disposed on an optical path of the laser beam traveling from the semiconductor laser to the dielectric block and reflects a part of the laser beam toward the semiconductor laser.

14. A surface plasmon sensor as defined in claim 11 in which the beam feedback optical system and the wavelength selector are formed by a fiber grating which reflects toward the semiconductor laser a rearward laser beam emitted from the semiconductor laser in the direction opposite to the laser beam traveling from the semiconductor laser to the dielectric block.

15. A surface plasmon sensor as defined in claim 1 in which the laser provided with an oscillation wavelength stabilizing means is a distributed feedback (DFB) laser.

16. A surface plasmon sensor as defined in claim 1 in which the laser provided with an oscillation wavelength stabilizing means is a distributed Bragg reflector (DBR) laser.

17. A surface plasmon sensor as defined in claim 1 in which the oscillation wavelength stabilizing means is a means for electrically controlling the oscillation wavelength of the laser.

18. A surface plasmon sensor as defined in claim 1 in which the dielectric block is shaped like a prism.

19. A surface plasmon sensor comprising:

a dielectric block;

a metal film which is formed on one side of the dielectric block and is brought into contact with a sample;

a laser emitting a light beam;

an optical system which causes the light beam to enter the dielectric block so that the light beam is reflected at an interface of the dielectric block and the metal film at an angle of incidence of the light beam to the interface, wherein the angle of incidence is an angle at which surface plasmon can be obtained;

a detector that detects the intensity of the light beam reflected from the interface; and an oscillation wavelength stabilizer that stabilizes the wavelength at which the laser oscillates.

20. A surface plasmon sensor as defined in claim 19 wherein the laser is a semiconductor laser and the light beam comprises a laser beam, and wherein the oscillation wavelength stabilizer comprises:

a beam feedback optical system which feeds a part of the light beam emitted from the laser back to the laser; and a wavelength selector which selects the wavelength of the light beam to be fed back to the laser.

21. A surface plasmon sensor as defined in claim 20 in which the wavelength selector comprises a bulk grating.

22. A surface plasmon sensor as defined in claim 21 in which the beam feedback optical system comprises:

a beam splitter which is disposed on an optical path of the laser beam traveling from the semiconductor laser to the dielectric block and splits a part of the laser beam; and a reflective grating which reflects the part of the laser beam split by the beam splitter to retrace its path, the reflective grating doubling as the wavelength selector.

23. A surface plasmon sensor as defined in claim 21 in which the beam feedback optical system and the wavelength selector are formed by a partial reflection type grating which is disposed on an optical path of the laser beam traveling from the semiconductor laser to the dielectric block and reflects a part of the laser beam toward the semiconductor laser.

24. A surface plasmon sensor as defined in claim 21 in which the beam feedback optical system and the wavelength selector are formed by a reflective grating which reflects toward the semiconductor laser a rearward laser beam emitted from the semiconductor laser in the direction opposite to the laser beam traveling from the semiconductor laser to the dielectric block.

25. A surface plasmon sensor as defined in claim 20 in which the wavelength selector comprises a narrow-band pass filter.

26. A surface plasmon sensor as defined in claim 25 in which the beam feedback optical system comprises:

a beam splitter which is disposed on an optical path of the laser beam traveling from the semiconductor laser to the dielectric block and splits a part of the laser beam; and a mirror which reflects the part of the laser beam split by the beam splitter to retrace its path, wherein the narrow-band pass filter is disposed on an optical path of the laser beam between the mirror and the semiconductor laser.

27. A surface plasmon sensor as defined in claim 25 in which the beam feedback optical system comprises:

a half-silvered mirror which is disposed on an optical path of the laser beam traveling from the semiconductor laser to the dielectric block and reflects a part of the laser beam toward the semiconductor laser, wherein the narrow-band pass filter is disposed on an optical path of the laser beam between the half-silvered mirror and the semiconductor laser.

28. A surface plasmon sensor as defined in claim 25 in which the beam feedback optical system comprises:

a mirror which reflects toward the semiconductor laser a rearward laser beam emitted from the semiconductor laser in the direction opposite to the laser beam traveling from the semiconductor laser to the dielectric block, wherein the narrow-band pass filter is disposed on an optical path of the rearward laser beam between the mirror and the semiconductor laser.

29. A surface plasmon sensor as defined in claim 20 in which the wavelength selector comprises a fiber grating which comprises an optical fiber having a plurality of refractive index varying portions formed in a core at regular intervals and reflects and diffracts a laser beam.

30. A surface plasmon sensor as defined in claim 29 in which the beam feedback optical system comprises:

a beam splitter which is disposed on an optical path of the laser beam traveling from the semiconductor laser to the dielectric block and splits a part of the laser beam; and a fiber grating which reflects the part of the laser beam split by the beam splitter to retrace its path, the fiber grating doubling as the wavelength selector.

31. A surface plasmon sensor as defined in claim 29 in which the beam feedback optical system and the wavelength selector are formed by a partial reflection type fiber grating which is disposed on an optical path of the laser beam traveling from the semiconductor laser to the dielectric block and reflects a part of the laser beam toward the semiconductor laser.

32. A surface plasmon sensor as defined in claim 29 in which the beam feedback optical system and the wavelength selector are formed by a fiber grating which reflects toward the semiconductor laser a rearward laser beam emitted from the semiconductor laser in the direction opposite to the laser beam traveling from the semiconductor laser to the dielectric block.

33. A surface plasmon sensor as defined in claim 19 in which the laser provided with an oscillation wavelength stabilizer is a distributed feedback (DFB) laser.

34. A surface plasmon sensor as defined in claim 19 in which the laser provided with an oscillation wavelength stabilizer is a distributed Bragg reflector (DBR) laser.

35. A surface plasmon sensor as defined in claim 19 in which the oscillation wavelength stabilizer can electrically control the oscillation wavelength of the laser.

36. A surface plasmon sensor as defined in claim 19 in which the dielectric block is shaped like a prism.

* * * * *